United States Patent
Kavusi et al.

(10) Patent No.: US 11,284,796 B1
(45) Date of Patent: Mar. 29, 2022

(54) ALIGNMENT DETECTION OF OPHTHALMIC CAMERA SYSTEM

(71) Applicant: Verily Life Sciences LLC, South San Francisco, CA (US)

(72) Inventors: Sam Kavusi, Menlo Park, CA (US); Eliezer Glik, San Francisco, CA (US); Honglei Wu, South San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 333 days.

(21) Appl. No.: 16/529,528

(22) Filed: Aug. 1, 2019

Related U.S. Application Data (60) Provisional application No. 62/724,299, filed on Aug. 29, 2018.

(51) Int. Cl.
| | |
|---|---|
| *A61B 3/15* | (2006.01) |
| *A61B 3/12* | (2006.01) |
| *A61B 3/00* | (2006.01) |
| *A61B 3/103* | (2006.01) |
| *A61B 3/107* | (2006.01) |

(52) U.S. Cl.
CPC ............... *A61B 3/152* (2013.01); *A61B 3/12* (2013.01); *A61B 3/156* (2013.01); *A61B 3/0008* (2013.01); *A61B 3/103* (2013.01); *A61B 3/107* (2013.01); *G06T 2207/30041* (2013.01)

(58) Field of Classification Search
CPC ........... A61B 3/152; A61B 3/12; A61B 3/156; A61B 3/103; A61B 3/107; A61B 3/0008; G06T 2207/30041

USPC .......................................................... 351/206
See application file for complete search history.

(56) References Cited

U.S. PATENT DOCUMENTS

| | | | |
|---|---|---|---|
| 7,216,985 B2 | 5/2007 | Siminou et al. | |
| 9,146,394 B1* | 9/2015 | Brillhart | G02B 25/001 |
| 9,271,649 B2 | 3/2016 | Wang | |
| 2011/0234977 A1* | 9/2011 | Verdooner | A61B 3/145 |
| | | | 351/207 |

FOREIGN PATENT DOCUMENTS

EP    0176169 A2    4/1986

OTHER PUBLICATIONS

Forus Health, 2017, 5 pages.
(Continued)

*Primary Examiner* — Mohammed A Hasan
(74) *Attorney, Agent, or Firm* — Christensen O'Connor Johnson Kindness PLLC (57) ABSTRACT

An ophthalmic camera system includes an eyepiece lens disposed in or on a housing. A flexible eyecup has a proximal opening end attached to the housing and surrounding the eyepiece lens and a distal opening end shaped to press against a face around an eye. An image sensor is adapted to acquire a retinal image of the eye through the eyepiece lens when the flexible eyecup is pressed against the face. A field source generates a field. A field sensing system senses the field. One of the field source or the field sensing system is disposed in or on the flexible eyecup and the other one is rigidly mounted to the housing. A controller is coupled to the field sensing system for tracking a relative position of the eyepiece lens relative to the field source to aid aligning the eyepiece lens to the eye.

24 Claims, 5 Drawing Sheets

(56) References Cited

OTHER PUBLICATIONS

Hannah L. Payne et al., "Magnetic eye tracking in Mice", elifesciences.org, Sep. 5, 2017, pp. 1-24.
Safaa Moqqaddem, et al. "Objects Detection and Tracking Using Points Cloud Reconstructed from Linear Stereo Vision", 2012, InTech, pp. 160-180.

* cited by examiner

ALIGNMENT DETECTION OF OPHTHALMIC CAMERA SYSTEM

CROSS REFERENCE TO RELATED APPLICATIONS

This application claims the benefit of U.S. Provisional Application No. 62/724,299, filed Aug. 29, 2018, which is hereby incorporated by reference in its entirety.

TECHNICAL FIELD

This disclosure relates generally to ophthalmic imaging technologies, and in particular but not exclusively, relates to alignment detection of an ophthalmic camera system.

BACKGROUND INFORMATION

Retinal imaging is a part of basic eye exams for screening, field diagnosis, and progress monitoring of many retinal diseases. A high fidelity retinal image is important for accurate screening, diagnosis, and monitoring. Bright illumination of the posterior interior surface of the eye (i.e., retina) through the pupil improves image fidelity but often creates optical aberrations or image artifacts, such as corneal reflections, iris reflections, or lens flare, if the retinal camera and illumination source are not adequately aligned with the eye. Simply increasing the brightness of the illumination does not overcome these problems, but rather makes the optical artifacts more pronounced, which undermines the goal of improving image fidelity.

Accordingly, camera alignment is very important, particularly with conventional retinal cameras, which typically have a very limited eyebox due to the need to block the deleterious image artifacts listed above. The eyebox for a retinal camera is a three dimensional region in space typically defined relative to an eyepiece of the retinal camera and within which the center of a pupil or cornea of the eye should reside to acquire an acceptable image of the retina. The small size of conventional eyeboxes makes retinal camera alignment difficult and patient interactions during the alignment process often strained.

Various solutions have been proposed to alleviate the alignment problem. For example, moving/motorized stages that automatically adjust the retina-camera alignment have been proposed. However, these stages tend to be mechanically complex and substantially drive up the cost of a retinal imaging platform. An effective and low cost solution for efficiently and easily achieving eyebox alignment of a retinal camera would improve the operation of retinal cameras.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system, apparatus, and method of operation for detecting alignment of an ophthalmic camera system are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
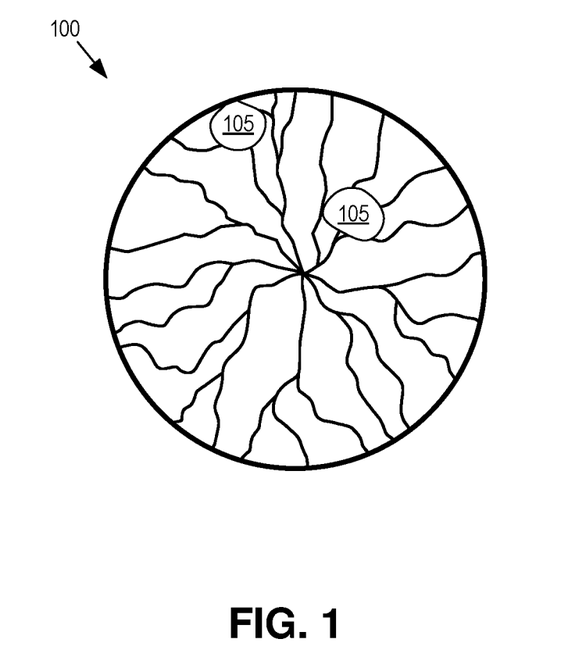
FIG. 1 illustrates a retinal image including an image artifact.

FIG. 1 illustrates an example retinal image 100 with multiple image artifacts 105. These image artifacts may arise when misalignment between the ophthalmic camera system and the eye permit stray light and deleterious reflections from the illumination source to enter the image path and ultimately are captured by the image sensor with the retinal image light. Misalignment can lead to deleterious corneal/iris reflections, refractive scattering from the crystalline eye lens, and occlusions of the imaging aperture.

High fidelity retinal images are important for screening, diagnosing, and monitoring many retinal diseases. Alignment of an ophthalmic camera system to a patient's eye can be difficult and misalignments result in poor quality retinal images with image artifacts that that occlude, or otherwise malign portions of the retinal images, as illustrated in FIG. 1. To this end, the ability to quickly, efficiently, and accurately align an ophthalmic camera system to acquire high quality retinal images with few or no image artifacts is desirable. Techniques that hasten the alignment phase of retinal imaging can reduce patient fatigue and reduce patient-practitioner tension.

Embodiments described herein include a magnetic tracking system that aids in quickly achieving gross alignment of the ophthalmic camera system with a patient's eye. The magnetic tracking system has a relatively lower computational overhead, as compared to a visual tracking system, and is capable of providing continuous, real-time feedback during the retinal imaging process. The magnetic tracking system is further capable of providing gross alignment feedback over a larger physical displacement than compared to a visual tracking system. While visual tracking systems, such as an iris tracker or a retinal tracker, can be highly accurate, these visual tracking systems are only functional over small physical displacements from the optimally aligned position (e.g., center of eyebox). As such, a visual tracking system alone cannot provide actionable alignment feedback outside a narrow displacement offset from the optical axis of the eye.

Due to the small size of the eyebox of most ophthalmic camera systems, precise alignment is required. Often, the patient's eye sweeps through the eyebox for a fleeting moment. Since visual tracking system can only provide alignment feedback in a small physical displacement from the center of the eyebox, the alignment feedback is often too late for the patient or the practitioner to timely react, resulting in frustratingly late corrections, or even overcorrections. The magnetic tracking system described herein is capable of providing early, actionable feedback. In various embodiments, the magnetic tracking system may be used in conjunction with a visual tracking system to provide both gross and fine alignment feedback as well as using the visual tracking system to calibrate a magnetic reference position (e.g., auto-zero) for the magnetic tracking system.

Figure 2A:
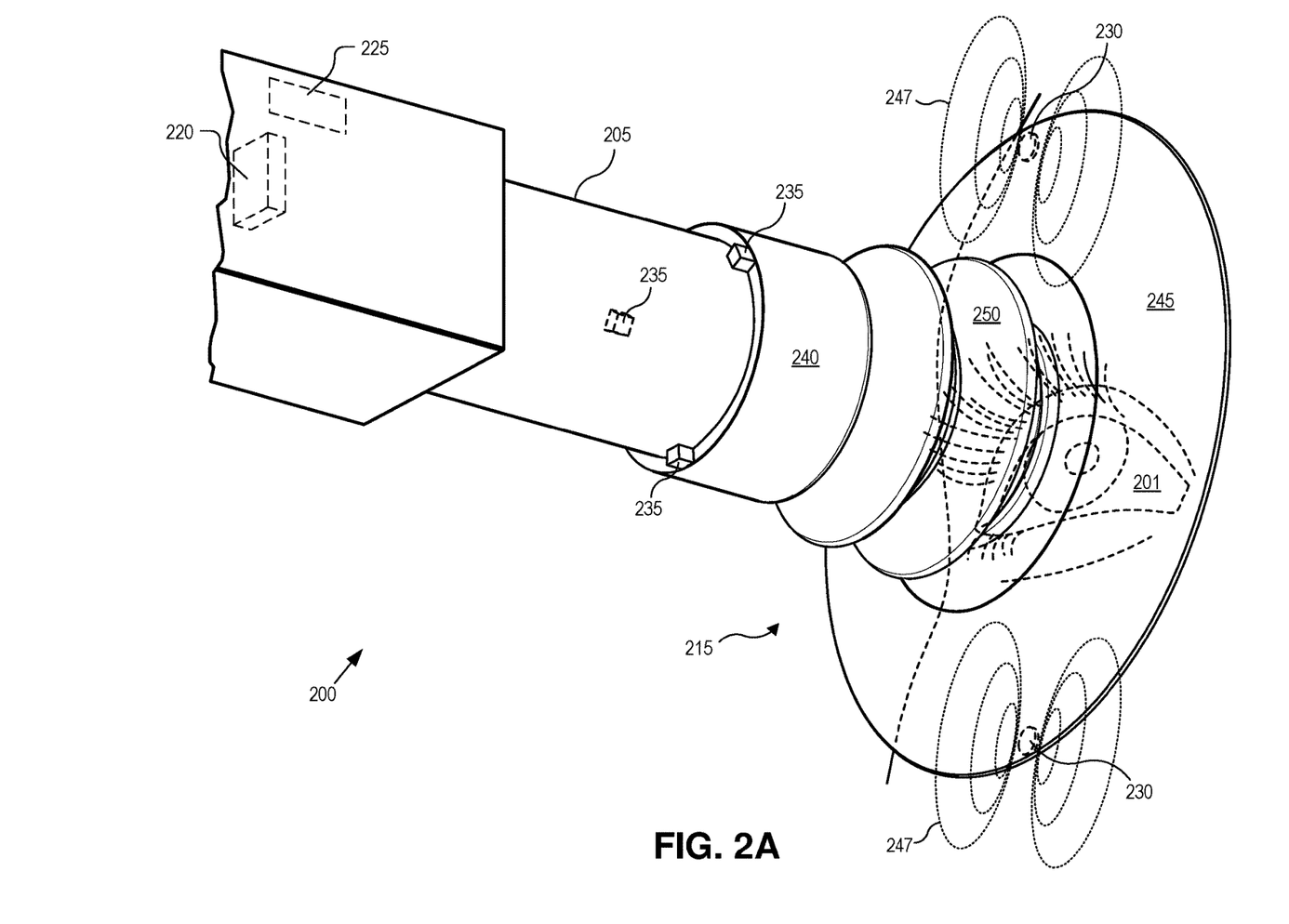
FIG. 2A is a perspective view illustration of a portion of an ophthalmic camera system having magnetic alignment sensing, in accordance with an embodiment of the disclosure.
Figure 2B:
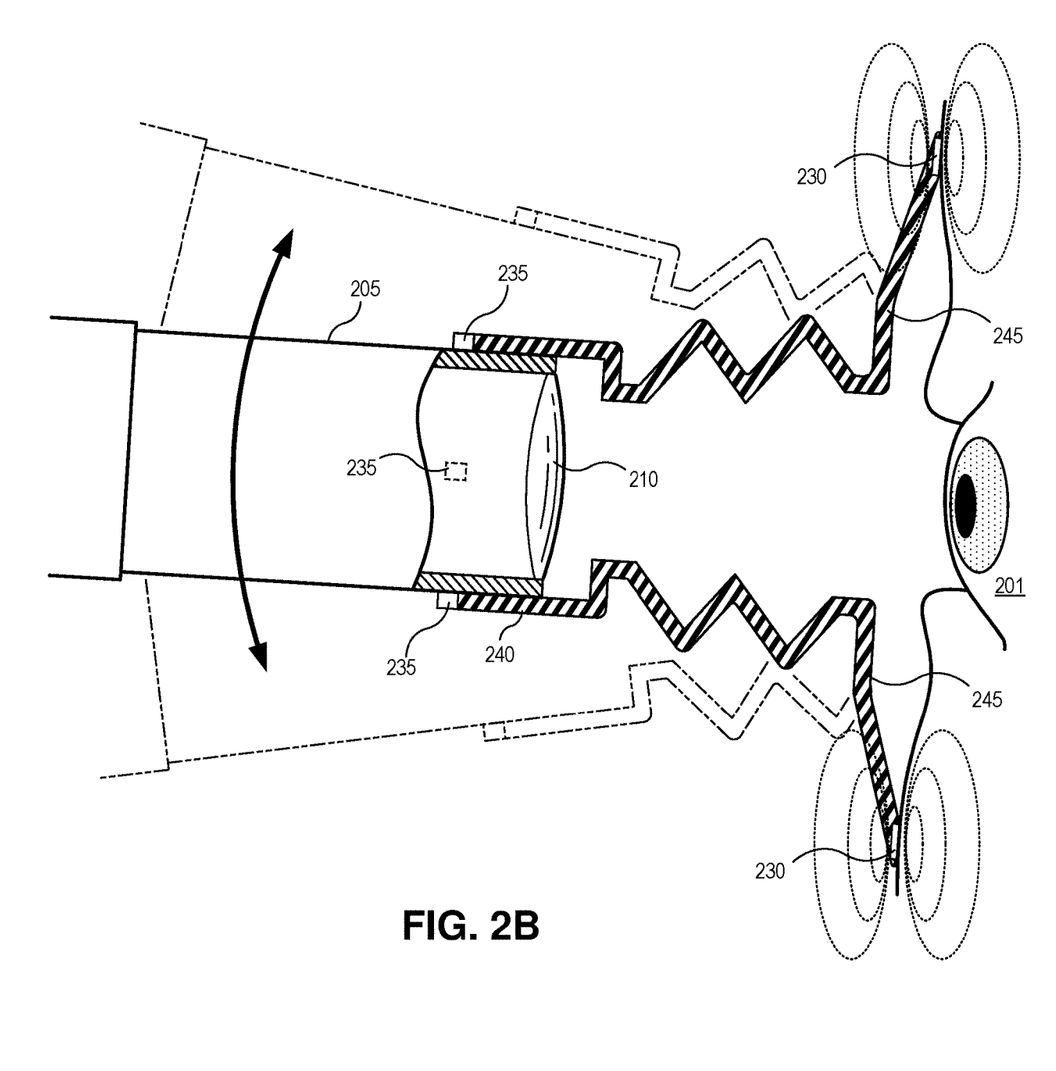
FIG. 2B is a cross-section illustration of a portion of an ophthalmic camera system having magnetic alignment sensing, in accordance with an embodiment of the disclosure.

FIGS. 2A and 2B illustrate a portion of an ophthalmic camera system 200 having magnetic alignment sensing, in accordance with an embodiment of the disclosure. FIG. 2A is a perspective view illustration while FIG. 2B is a cross-section view illustration of the same. The illustrated embodiment of system 200 includes a housing 205, an eyepiece lens 210 (see FIG. 2B), a flexible eyecup 215, an image sensor 220, a controller 225, magnetic sources 230, and a magnetic sensing system including magnetic sensors 235. The illustrated embodiment of flexible eyecup 215 includes a proximal opening end 240, a distal opening end 245, and a baffled section 250.

Proximal opening end 240 of flexible eyecup 215 is attached to the housing 205 and surrounds eyepiece lens 205. Distal opening end 245 is shaped and sized to press against a user's face around eye 201. Flexible eyecup 215 may be fabricated of a soft, flexible, opaque material (e.g., rubber, silicon, etc.) that can be comfortably pressed against the user's face to form a contact point between the face and the ophthalmic camera system 200. In the illustrated embodiment, distal opening end 245 includes a flange that flexibly conforms to the user's forehead and check around eye 201 to block out light. The rubberized material of flexible eyecup 215 may also provide sufficient friction to the user's skin to provide a substantially fixed position relative to the face when flexible eyecup 215 is pressed against the face to permit pivoting of housing 205 relative to the face during the alignment process without distal opening end 245 moving relative to the face (e.g., see FIG. 2B). In one embodiment, distal opening end 245 may include a tactile, non-slip, or adhesive coating or surface for pressing against the face to reduce the likelihood of slippage during alignment. Baffle section 250 permits the adjustment of a translation offset (e.g., eye relief 301 illustrated in FIG. 3) between eyepiece lens 205 and eye 201 while maintaining pressure at distal opening end 245 against the face to maintain a fixed, light seal around eye 201. In the illustrated embodiment, proximal opening end 240 forms a gasket-like seal around the tubular portion of housing 205, which includes eyepiece lens 205. Other shapes or mechanical connection form factors for proximal opening end 240 may be implemented.

Flexible eyecup 215 includes magnetic sources 230 disposed in or on distal opening end 245 to generate magnetic fields 247. Although FIGS. 2A & B illustrate two magnetic sources 230 as an example, one or more magnetic sources 230 may be used. Magnetic sources 230 are disposed at or near distal opening end 245 of flexible eyecup 215 so that they maintain a substantially fixed position relative to the face when flexible eyecup 215 is pressed against the face and while housing 205 is pivoted and/or translated relative to eye 201 to achieve alignment. For example, the flexibility of baffle section 250 permits housing 205 to be physically manipulated to achieve alignment all while distal opening end 245 and magnetic sources 230 hold a substantially fixed position relative to the face. Housing 205 can be pivoted in multiple degrees of freedom (e.g., two pivoting degrees of freedom) and even translated to adjust an offset (e.g., eye relief) while magnetic sources 230 remain fixed on the patient's face. FIG. 2B illustrates how housing 205 can be pivoted up and down relative to the face without moving magnetic sources 230 relative to the face. In one embodiment, magnetic sources 230 are implemented using permanent magnets. In other embodiments, electromagnets may be used.

Magnetic field 247 output from magnetic sources 230 is sensed by magnetic sensors 235 of the magnetic sensing system. Changes in the sensed magnetic field 247 correlate to physical changes in the relative position between magnetic sources 230 and magnetic sensors 235. Changes in the relative position between magnetic sources 230 and magnetic sensors 235 are correlated to changes in the relative position of eyepiece lens 205 to the face since magnetic sensors 235 have a rigid (fixed) position relative to eyepiece lens 205 and magnetic sources 230 have a fixed position relative to the face when flexible eyecup 215 is pressed against the face (despite physical changes in the position of housing 205 while adjusting camera alignment). By monitoring and tracking these changes, real-time feedback about the relative position can be provided to aid the gross alignment process. Real-time feedback can be provided as prompts instructing how to manipulate housing 205 relative to the face to improve alignment. For example, the real-time feedback may include audible feedback and/or visual cues.

The magnetic sensing system may include one or more sensors to sense and track one or more degrees of freedom of movement of housing 205. In the illustrated embodiment, the magnetic sensing system includes multiple magnetic sensors 235 (e.g., three sensors) disposed in or on housing 205 and offset from each other to sense movement in multiple degrees of freedom. The offset set positioning enables the implementation of triangulation principles to measure multiple degrees of freedom. In one embodiment, enough magnetic sensors 235 are provided to sense at least two pivoting degrees of freedom of housing 205 and one translational offset of housing 205 relative to magnetic sources 230, and by extension relative to the face. In the illustrated embodiment, magnetic sensors 235 are positioned close to flexible eyecup 215 to increase the strength of magnetic fields 247 at their position and to reduce the influences of external magnetic fields.

A number of modifications to the illustrated architecture may be implemented within the spirit of the instant disclosure. For example, the relative positions of magnetic sources 230 and magnetic sensors 235 may be swapped. In this alternative embodiment, one or more magnetic sources 230 may be disposed in or on housing 205 while one or more magnetic sensors 235 may be disposed in or on distal opening end 245 of flexible eyecup 215 and electronic signal/power lines run within flexible eyecup 215 to housing 205. Furthermore, magnetic sensors 235 may be positioned in a variety of positions and relative orientations about housing 205. In one embodiment, magnetic sensors 235 may even be disposed within proximal opening end 240 of flexible eyecup 215 and electrically powered by contact connections to housing 205. In embodiments where magnetic sensors 235 are disposed in distal opening end 240, the magnetic sensors 235 are still deemed to be disposed on housing 205 since distal opening end 240 is in direct and rigid contact with housing 205 so that the relative position of magnetic sensors 235 and housing 205 do not change during operation.

Magnetic sensors 235 may be implemented using a variety of magnetic sensing technologies. For example, in one embodiment, magnetic sensors 235 are implemented using Hall Effect sensors; however, other types of magnetic sensors may be used. Furthermore, magnetic sensors 235 and magnetic sources 230 may generically be referred to as field sensors 235 and field sources 230 as other types of electromagnetic fields may be used to achieve the desired field tracking. For example, magnetic sources 230 may be replaced by light sources and magnetic sensors 235 may be replaced by light sensors. Similarly, magnetic sources 230 may be replaced by electrostatic sources (e.g., electrets) while magnetic sensors 235 may be replaced by an electrostatic field sensor. In yet other embodiments, magnetic sources 230 may be replaced with dynamic (e.g., modulated) field generators, field reflectors, or otherwise. In yet other embodiments, ultrasonic generators and sensors may also be used. The terminology field source and field sensing system are broadly defined herein to encompass all of these alternatives.

Figure 3:
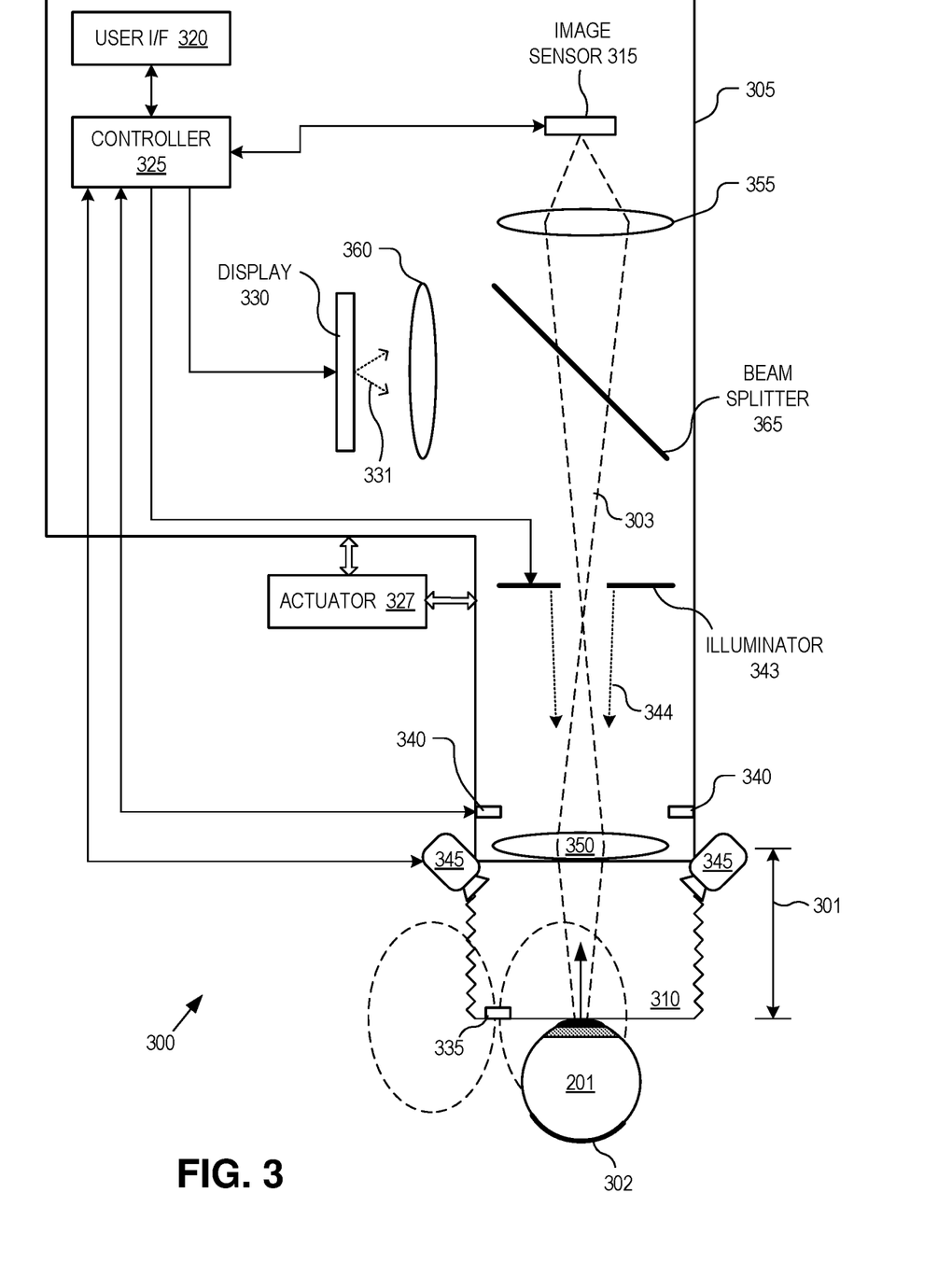
FIG. 3 illustrates components of an ophthalmic camera system having a magnetic alignment system, in accordance with an embodiment of the disclosure.

FIG. 3 illustrates functional components of an ophthalmic camera system 300 having a magnetic alignment system, in accordance with an embodiment of the disclosure. System 300 is one possible implementation of system 200 illustrated in FIGS. 2A and 2B. The illustrated embodiment of system 300 includes a housing 305, flexible eyecup 310, an image sensor 315, a user interface 320, a controller 325, a display 330, magnetic source 335, magnetic sensors 340, an illuminator 343, a visual eye tracking system, and an optical relay system. The visual eye tracking system may include one or more of display 330, image sensor 315, or iris cameras 345. The optical relay system includes eyepiece lens 350, lenses 355 and 360, and a beam splitter 365.

Illuminator 343 generates illumination light 344 for illuminating retina 302 of eye 201. In one embodiment, illuminator 343 is a ring illuminator having a center aperture through which retinal image light 303 passes before being captured as a retinal image by image sensor 315. The aperture serves to block deleterious off axis reflections/refractions from the cornea, iris, and/or crystalline lens of eye 201. Beam splitter 365 is positioned to pass a portion of the light 303 to image sensor 315 while reflecting display light 331 output from display 330 to eye 201. Display light 331 may include a fixation target or other visual cues to aid retinal alignment during imaging. In some embodiments, beam splitter 365 is more transmissive than reflective. In one embodiment, beam splitter 365 is approximately 90% transmissive and 10% reflective. Other reflectance/transmittance ratios may be implemented. Lens systems 350, 355, and 360 are provided throughout system 300 to provide image and light focusing in the optical paths.

User interface 320 provides a mechanism for interfacing with system 300. User interface 320 may include both input and output mechanisms. For example, user interface 320 may include a speaker to provide audible feedback. In one embodiment, display 330 may be considered a subcomponent of user interface 320 as it provides a fixation target and/or visual cues to the patient through eyepiece lens 350 during alignment. User interface 320 may also include an external display for viewing by a practitioner.

In the illustrated embodiment, controller 325 is coupled to image sensor 315, user interface 320, display 330, illuminator 343, iris cameras 345, and the magnetic sensing system to choreograph their operation. Controller 325 may include software/firmware logic executing on a microcontroller, hardware logic (e.g., application specific integrated circuit, field programmable gate array, etc.), or a combination of software and hardware logic. Although FIG. 3 illustrates controller 325 as a distinct functional element, the logical functions performed by controller 325 may be decentralized across a number hardware elements.

Figure 4:
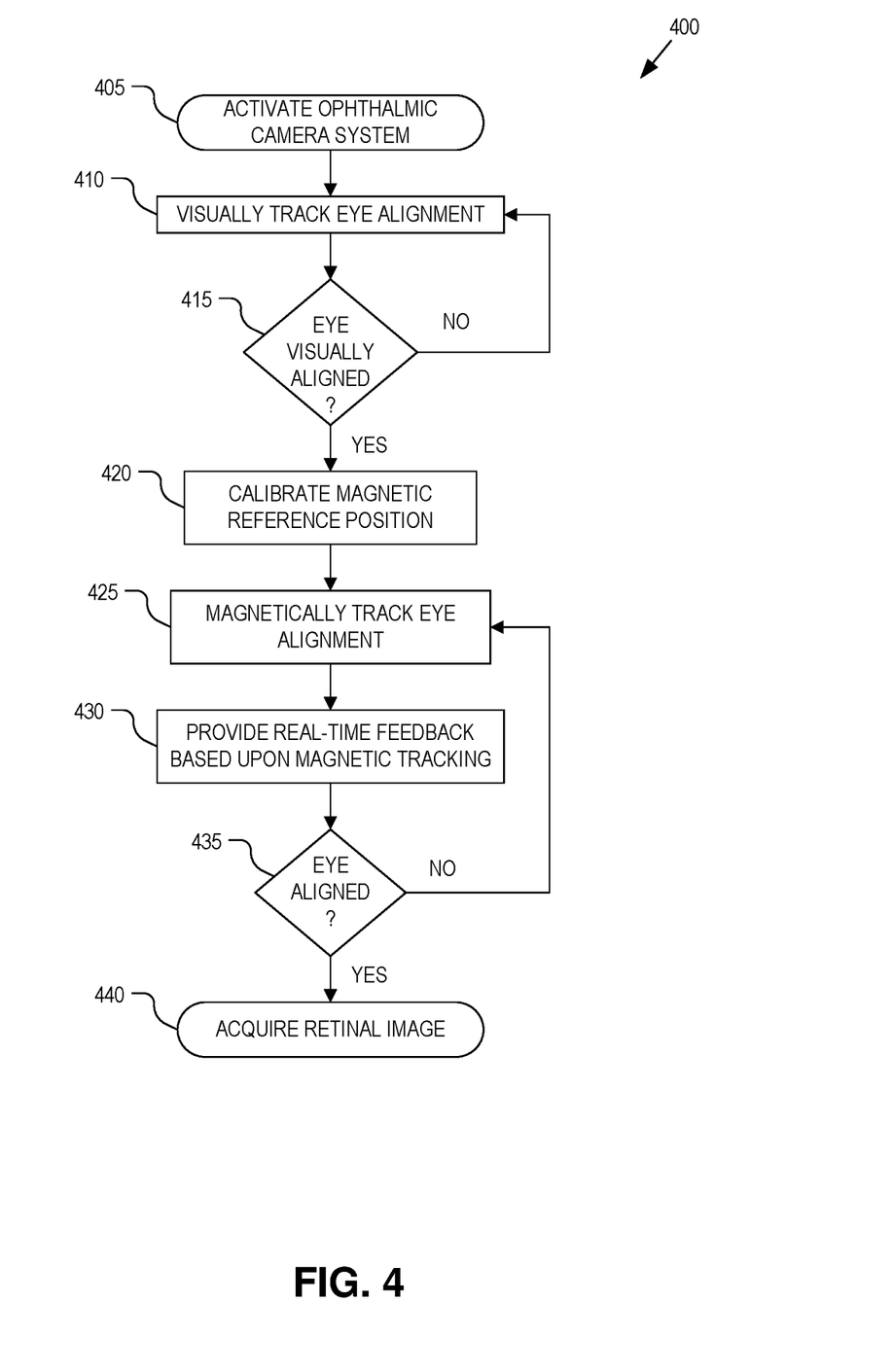
FIG. 4 is a flow chart illustrating a process of operation of the ophthalmic camera system to achieve alignment and acquire a retinal image, in accordance with an embodiment of the disclosure.

FIG. 4 is a flow chart illustrating a process 400 of operation of ophthalmic camera system 300 (or 200) to achieve alignment and acquire a retinal image, in accordance with an embodiment of the disclosure. The order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel.

In a process block 405, ophthalmic camera system 300 is activated. Activation may be achieved with user interface 320. Once activated, the visual and magnetic tracking systems are enabled. In process block 410, the visual tracking system commences visually tracking eye alignment. The visual tracking system may be implemented using iris cameras 345, which track the position of the iris or retina of eye 201. Alternatively, the visual tracking system may use image sensor 315 (other another image sensor not illustrated) to perform retinal tracking of retina 302 through eyepiece 350. Although visual tracking provides high accuracy, it generally only works within a small physical displacement of the eyebox. As such, eyepiece lens 350 will often sweep through the eyebox too quickly to acquire a retinal image. However, this sweep through the eyebox is not too fast to calibrate a magnetic reference position (e.g., zero-out) the magnetic tracking system.

Accordingly, in a decision block 415, the visual tracking system is operated by controller 325 to identify even brief moments of alignment between eyepiece lens 350 and eye 201. When eye 201 is deemed to be visually aligned with eyepiece lens 350 (decision block 415), controller 325 calibrates the magnetic reference position of the magnetic sensing system (process block 420). Calibration may include time synchronizing the capture of magnetic field readings output from magnetic sensors 340 with images or data acquired by the visual tracking system. The determination of visual alignment may be real-time, or can be delayed as long as the magnetic sensor values are captured and recorded in sync with the iris or retinal images for subsequent analysis.

Once the magnetic reference position corresponding to eyebox alignment has been calibrated (process block 420), the magnetic tracking system can commence magnetically tracking eye alignment based upon the magnetic field output from magnetic sources 335 (process block 425). With the magnetic tracking system activated, real-time feedback for gross alignment based upon the magnetic tracking commences (process block 430). This gross alignment feedback provides real-time feedback to the patient and/or practitioner over a larger physical displacement than the visual tracking system is capable of doing. In one embodiment, the commencement of magnetic tracking and real-time feedback prompts are automatic and seamless to the user/practitioner.

The real-time feedback is provided by user interface 320 (which may include display 330 in some embodiments). The real-time feedback may simply provide information about the relative position of eyepiece lens 350 and the user's face. This feedback information may be used to aid aligning eyepiece lens 350 to eye 201. In one embodiment, the real-time feedback includes prompts instructing how to manipulate housing 305 relative to the face to improve the alignment. Example prompts may include tilt up, tilt down, tilt left, tilt right, move closer, move away, etc. In one embodiment, user interface 320 may provide the real-time feedback as audible feedback through a speaker. In one embodiment, user interface 320 may provide the real-time feedback as visual cues (e.g., arrows, various alignment symbols, dynamic changes in a fixation target, etc.) output from display 330. In yet another embodiment, both visual and audible cues may be generated. In some embodiments, user interface 320 may include an external display providing the visual cues to the practitioner instead of (or in concert with) cues provided to the patient through eyepiece lens 350.

Accordingly, controller 325 monitors the feedback signals from magnetic sensors 340 to not only track and determine a relative position between eyepiece lens 350 and eye 201, but also uses knowledge of the relative position from the magnetic tracking system to determine the relative direction of movement needed to improve alignment. This real-time corrective feedback or correction action may be provided to the user (patient or practitioner), as described above, for manual corrective action, or may be provided to an actuator (e.g., actuator 327) for automated alignment. The actuator may be an electro-optical adjustable lens system, an electro-mechanical system (motors, servos, etc.), or otherwise. The actuator may be coupled to physically manipulate housing 205, eyepiece lens 210, or other optical elements within the camera system.

The magnetic tracking system provides timely, actionable alignment related feedback over a larger physical displacement from the center of the eyebox, which aids in achieving a more steady alignment for a period of time of sufficient duration to acquire a retinal image. When alignment is achieve (decision block 435), the retinal image(s) are acquired by image sensor 315 and stored by controller 325. In one embodiment, the determination of alignment for the purposes of image acquisition may be executed based upon the visual tracking system given its potential for greater precision. In yet other embodiments, the magnetic tracking system may be referenced for determining alignment and triggering image acquisition.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic camera system, comprising:
a housing;
an eyepiece lens disposed in or on the housing;
a flexible eyecup having a proximal opening end attached to the housing and surrounding the eyepiece lens and a distal opening end shaped to press against a face around an eye;
an image sensor optically aligned with the eyepiece lens to acquire a retinal image of the eye through the eyepiece lens when the flexible eyecup is pressed against the face;
a field source to generate a field;
a field sensing system to sense the field from the field source, wherein either one of the field source or the field sensing system is disposed in or on the flexible eyecup and the other one of the field source or the field sensing system is rigidly mounted to the housing; and
a controller coupled to the field sensing system, the controller including logic that when executed by the controller causes the ophthalmic camera system to track, based on an output of the field sensing system, a relative position of the eyepiece lens to the field source to aid aligning the eyepiece lens to the eye.

2. The ophthalmic camera system of claim 1, further comprising:
a user interface coupled to the controller, wherein the controller includes further logic that when executed by the controller causes the user interface to output real-time feedback about the relative position to aid aligning the eyepiece lens to the eye.

3. The ophthalmic camera system of claim 2, wherein the real-time feedback comprises prompts instructing how to manipulate the housing relative to the face to improve an alignment of the eyepiece lens to the eye.

4. The ophthalmic camera system of claim 2, wherein the user interface comprises at least one of:
a speaker to output the real-time feedback as audible feedback; or
an alignment display optically coupled to the eyepiece lens to output the real-time feedback as visual cues to the eye.

5. The ophthalmic camera system of claim 1, wherein either the field source or the field sensing system is disposed in or on the flexible eyecup adjacent to the distal opening end of the flexible eyecup such that either the field source or the field sensing system holds a substantially fixed position relative to the face when the flexible eyecup is pressed against the face and while pivoting the housing relative to the face.

6. The ophthalmic camera system of claim 5, further comprising:

a plurality of field sources, including the field source, disposed in or on the flexible eyecup about the distal opening end.

7. The ophthalmic camera system of claim 1, wherein the field source comprises a permanent magnet and the field comprises a magnetic field.

8. The ophthalmic camera system of claim 1, wherein the field sensing system comprises:
a plurality of magnetic sensors disposed in or on the housing and offset from each other to sense the relative position in multiple degrees of freedom.

9. The ophthalmic camera system of claim 8, wherein the magnetic sensors are arranged to sense two pivoting degrees of freedom of the housing relative to the face and a translational offset between the housing and the face when the flexible eyecup is pressed against the face.

10. The ophthalmic camera system of claim 1, further comprising:
an eye tracking system coupled to the controller, and wherein the controller includes further logic that when executed by the controller causes the ophthalmic camera system to perform operations including:
visually tracking the eye with the eye tracking system;
determining when the eyepiece lens is aligned, within a threshold, to the eye based upon the visual tracking; and
calibrating a magnetic reference position for magnetic tracking with the field sensor system in response to determining the eyepiece lens is aligned with the eye tracking system.

11. The ophthalmic camera system of claim 10, wherein the eye tracking system comprises at least one of a retinal camera mounted for retinal tracking or an iris camera mounted for iris or pupil tracking.

12. The ophthalmic camera system of claim 1, wherein the controller includes further logic that when executed by the controller causes the ophthalmic camera system to perform further operations comprising:
determining a direction of motion, based at least in part upon the output of the field sensing system, that provides corrective motion for improving an alignment of the ophthalmic camera system with the eye; and
generating a corrective feedback signal that indicates the direction of motion.

13. The ophthalmic camera system of claim 12, further comprising:
an actuator coupled to the controller to receive the corrective feedback signal, the actuator adapted to manipulate the housing or the eyepiece lens to improve the alignment between the eyepiece lens and the eye in response to the corrective feedback signal.

14. A method of operation of an ophthalmic camera system having an eyepiece lens disposed in or on a housing, the method comprising:
sensing a magnetic field output from a magnetic source disposed in or on a flexible eyecup, the flexible eyecup having a proximal opening end attached to the housing and surrounding the eyepiece lens and a distal opening end shaped to press against a face around an eye;
tracking changes in a relative position of the eyepiece lens to the face based upon the magnetic field; and
acquiring a retinal image of the eye when the eyepiece lens is determined to be aligned with the eye.

15. The method of operation of claim 14, further comprising:
outputting real-time feedback about the relative position based upon the tracking to aid aligning the eyepiece lens to the eye.

16. The method of operation of claim 15, wherein outputting the real-time feedback comprises:
generating prompts instructing how to manipulate the housing relative to the face to improve an alignment of the eyepiece lens to the eye.

17. The method of operation of claim 16, wherein real-time feedback about the relative position comprises at least one of:
an audible feedback; or
a visual cue displayed to the eye through the eyepiece lens.

18. The method of operation of claim 14, wherein the magnetic source is disposed in or on the flexible eyecup adjacent to the distal opening end of the flexible eyecup such that the magnetic source holds a substantially fixed position relative to the face when the eyecup is pressed against the face and while pivoting the housing relative to the face.

19. The method of operation of claim 14, wherein sensing the magnetic field comprises:
sensing the magnetic field with a plurality of magnetic sensors disposed in or on the housing and offset from each other to sense the relative position in multiple degrees of freedom.

20. The method of operation of claim 19, wherein tracking changes in the relative position of the eyepiece lens to the face based upon the magnetic field comprises:
tracking two pivoting degrees of freedom of the housing relative to the face; and
tracking a translational offset between the housing and the face when the flexible eyecup is pressed against the face.

21. The method of operation of claim 14, further comprising:
visually tracking the eye;
determining when the eyepiece lens is aligned, within a threshold, to the eye based upon the visual tracking; and
calibrating a magnetic reference position for the tracking based upon the magnetic field in response to determining that the eyepiece lens is aligned based upon the visual tracking.

22. The ophthalmic camera system of claim 21, wherein the visual tracking comprises at least one of tracking a retinal position of the eye through the eyepiece lens or tracking an iris position of the eye.

23. An ophthalmic camera system, comprising:
a housing;
an eyepiece lens disposed in or on the housing;
a flexible eyecup having a proximal opening end attached to the housing and surrounding the eyepiece lens and a distal opening end shaped to press against a face around an eye;
an image sensor optically aligned with the eyepiece lens to acquire a retinal image of the eye through the eyepiece lens when the flexible eyecup is pressed against the face; and
a feedback alignment mechanism at least partially integrated into the flexible eyecup to provide the user with real-time gross alignment feedback indicating whether the eyepiece lens is in near alignment with the eye or is farther out of alignment with the eye.

24. The ophthalmic camera system of claim 23, wherein the feedback alignment mechanism comprises:
a field source to generate a field;

a field sensing system to sense the field from the field source, wherein either one of the field source or the field sensing system is disposed in or on the flexible eyecup and the other one of the field source or the field sensing system is rigidly mounted to the housing; and
a controller coupled to the field sensing system, the controller including logic that when executed by the controller causes the ophthalmic camera system to track, based on an output of the field sensing system, a relative position of the eyepiece lens to the field source to aid aligning the eyepiece lens to the eye.

* * * * *